US012376982B2

(12) United States Patent
Granieri (10) Patent No.: US 12,376,982 B2
(45) Date of Patent: Aug. 5, 2025

(54) SPHERICAL JOINT MOBILIZATION BRACE

(71) Applicant: Fabrizio Granieri, Trani (IT)

(72) Inventor: Fabrizio Granieri, Trani (IT)

( * ) Notice: Subject to any disclaimer, the term of this patent is extended or adjusted under 35 U.S.C. 154(b) by 857 days.

(21) Appl. No.: 17/425,051

(22) PCT Filed: Jan. 16, 2020

(86) PCT No.: PCT/IB2020/050344
§ 371 (c)(1),
(2) Date: Jul. 22, 2021

(87) PCT Pub. No.: WO2020/152549
PCT Pub. Date: Jul. 30, 2020

(65) Prior Publication Data
US 2022/0096259 A1    Mar. 31, 2022

(30) Foreign Application Priority Data

Jan. 23, 2019 (IT) .................. 102019000001003

(51) Int. Cl.
*A61F 5/01* (2006.01)
(52) U.S. Cl.
CPC ............ *A61F 5/013* (2013.01); *A61F 5/0123* (2013.01); *A61F 5/0127* (2013.01);
(Continued)
(58) Field of Classification Search
CPC ........ A61F 5/01; A61F 5/0102; A61F 5/0111; A61F 5/0118; A61F 5/013; A61F 5/0127;
(Continued)

(56) References Cited

U.S. PATENT DOCUMENTS

| 5,547,464 A * | 8/1996 | Luttrell ................. A61H 1/024 482/111 |
| 2004/0002674 A1* | 1/2004 | Sterling ................ A61F 5/0123 602/26 |

(Continued)

FOREIGN PATENT DOCUMENTS

JP          2012235928 A  *  12/2012

OTHER PUBLICATIONS

Machine translation of Publication No. JP2012235928A created Jun. 6, 2024 from Espacenet [retrieved from https://worldwide.espacenet.com/patent/search/family/047459410/publication/JP2012235928A?q=JP2012235928] (Year: 2012).*

*Primary Examiner* — Ophelia A Hawthorne
*Assistant Examiner* — Gina McCarthy
(74) *Attorney, Agent, or Firm* — R. Ruschena Patent Agent, LLC (57) ABSTRACT

A device for articular rehabilitation comprising a first element provided with bars for fastening to the proximal portion of a limb and a second element provided with bars for fastening to the distal portion of a limb, said first element comprising a first and a second spherical shell portion opposite to each other, and said second element comprising a first and a second spherical shell portion opposite to each other, said spherical shell portions being configured to fasten said first and second element by means of spherical hinge coupling and being configured so that the space comprised inside said spherical shell portions, when coupled, is such that the joint object of the rehabilitation is allowed to be received therein.

10 Claims, 9 Drawing Sheets

(52) U.S. Cl.
CPC ............... *A61F 2005/0137* (2013.01); *A61F 2005/0144* (2013.01); *A61F 2005/0146* (2013.01)

(58) Field of Classification Search
CPC .... A61F 5/023; A61F 5/04; A61F 5/05; A61F 5/05858; A61F 5/05866; A61F 5/373; A61F 5/3723; A61F 5/3761; A61F 2005/0132; A61F 2005/0134; A61F 2005/0137; A61F 2005/0144; A61F 2005/0146; A61F 2005/0148; A61F 2005/0151; A61F 2005/0153; A61F 2005/0155; A61F 2005/0165; A61F 13/06; A61F 13/061; A61H 2001/0203; A61H 1/02; A61H 1/0277; A61H 2201/0153; A61H 2201/0173; A61H 2201/1215; A61H 2201/123; A61H 2201/1635; A61H 2201/165; A61H 1/024; A61H 1/0237; A63B 23/035; A63B 23/03508; A63B 23/12; A63B 23/1281
USPC ............... 602/5, 20, 27; 128/878, 881, 892
See application file for complete search history.

(56) References Cited

U.S. PATENT DOCUMENTS

2018/0015284 A1* 1/2018 Coleman ............... G16H 40/63
2018/0325766 A1* 11/2018 Arzanpour ........... A61H 1/0237

* cited by examiner

SPHERICAL JOINT MOBILIZATION BRACE

BACKGROUND OF THE INVENTION

Field of the Invention

Object of the present invention is an orthopedic immobilization brace apt to the rehabilitation of human body joints, in particular the elbow one, but also the knee, ankle, and shoulder ones as well.

Brief Description of the Prior Art

It is known that after surgery or a trauma, in order to restore the correct articular function, it is needed to carry out rehabilitation movements. In particular, in case of the rehabilitation of the elbow joint, it is also needed to carry out repeatedly flexion and extension exercises combined with movements lying on one's stomach/on one's back. At the state of the art, various machines are known allowing to carry out this kind of movements in a guided way, both passively (with the machine which, by means of a motorized system, carries out the exercise) and in actively (with the patient who has to exert the force needed to carry out the exercise).

By analyzing, for simplicity, the case of the rehabilitation of the elbow it is to be highlighted that many examples of devices are known at the state of the art for rehabilitation, which are configured to be fastened to the patient arm and forearm and to allow to carry out arm flexion and extension movements in a guided way. Some not limiting examples are described in CN103251493, CN103536426, CN103976852A, MI2010A001769.

Anyway, these and other devices known at the state of the art are limited since the kinematism implemented does not allow to make the joint center of the instantaneous rotation and the kinematism center of instantaneous rotation coincide constantly during the whole extension movement, and since they eliminate completely the possibility of forearm rotation around its own axis (on one's stomach/on one's back).

In fact, it is known that the elbow joint, even if for simplicity it is often schematized as a cylinder hinge arranged between arm and forearm, it is actually a complex kinematism, and during flexion/extension movements (combined with the ones lying on one's stomach/on one's back) the center of instantaneous rotation does not remain constant. By imposing by means of an outer device that the rotation center is constant (as, it occurs actually in all the devices having a cylinder hinge between arm and forearm, the execution of the exercise becomes other than what would be the natural movement without the brace.

In addition to the variation of the rotation center, in the natural movement of the forearm, during flexion/extension, a slight rotation around its own axis (on one's stomach/on one's back) is observed. Generally, it can be said that in a joint it is possible to individuate a main rotation axis (which however corresponds to the unique movement allowed by the devices known at the state of the art), but such rotation axis is not the only one, since the joint allows movements—even if of lower angular extension—around other axes. By avoiding minor rotations by forcing the joint to move like a cylinder hinge the benefits of the rehabilitation therapy are reduced.

Another limit of the devices known at the state of the art is also the fact that the they are either completely passive (they do not help the patient to exert forces, but they guide the movement only) or completely active (they exert a constant force during the whole exercise) For an efficient rehabilitation it is preferred instead that the patient is helped to carry out the movement (by applying a suitable force) only for those movement portions that the patient is not able to carry out by himself. It is clear that, while the rehabilitation progresses, the amplitude of the movement that the patient is able to carry out by himself increases, up to coincide with the whole extension of the movement. Therefore, a rehabilitation device has to allow to vary the movement portion which the patient is helped to do by the device.

SUMMARY OF THE INVENTION

Therefore, aim of the present invention is to provide a device for the orthopedic rehabilitation, which overcomes the limits of the devices known at the state of the art.

More in particular, the present invention provides a device for articular rehabilitation which allows to carry out the rehabilitation exercises by favouring the natural joint kinematism, and in particular by following constantly the center of instantaneous rotation.

Yet, the present invention provides a device for the orthopedic rehabilitation in which the relative movement allowed to the joint (for example to the forearm with respect to the arm, rather than to the tibia with respect to the femur) allows also rotations around its own axis, in addition to the ones around the main rotation axis of the joint.

According to another aim, the present invention provides a device for the orthopedic rehabilitation comprising a spherical hinge configured to keep its own rotation center constantly at the instantaneous rotation center of the joint, which combines movements of flexion, extension and while lying on one's stomach/on one's back.

Yet, the present invention provides an orthopedic brace provided with means for exerting forces apt to help to carry out the movement, configured so that said forces can be exerted alternatively for the whole execution of the movement, for a part of the same or so that they are not exerted at all.

Finally, the present invention provides an orthopedic brace which has all the just described advantages, and which is however simple and cheap to be realized, and which has little dimensions as well, so that it can be transported and worn simply by the patient.

Yet, another aim of the invention is to provide a device which can be used as an exoskeleton, while keeping all the just described advantages.

The present invention realizes the prefixed aims since it is a device (1) for articular rehabilitation comprising a first element (2) provided with bars (24, 25) for fastening to the proximal portion of a limb and a second element (3) provided with bars (34, 35) for fastening to the distal portion of a limb, said first element (2) comprising a first (21) and a second spherical shell portion (22) opposite to each other, and said second element (3) comprising a first (31) and a second spherical shell portion (32) opposite to each other, said spherical shell portions (21, 22, 31, 32) being configured to fasten said first and second element by means of spherical hinge coupling and being configured so that the space comprised inside said spherical shell portions (21, 22, 31, 32), when coupled, is such that the joint object of the rehabilitation is allowed to be received therein, said first (21, 31) and second spherical shell portion (22, 32) of each one of the two elements (2, 3) being firmly connected to each other and configured to be positioned on opposite portions of the joint when said device (1) is worn, said first spherical shell portion (21) of said first element (2) being configured to be coupled with said first spherical shell portion (31) of said second element (3), and said second spherical shell portion (22) of said first element (2) being configured to be coupled with said second spherical shell portion (32) said second element (3).

DETAILED DESCRIPTION OF THE INVENTION

These and other advantages will be clear from the detailed description of the invention, which will be carried out in the following with reference to the appended FIGS. 1 to 19.

Firstly, it is to be specified that even if for explanation simplicity the device is shown in the figures and described in the text for its usage for the elbow rehabilitation, with suitable modifications which the expert in the field will be able to implement without inventive effort, the device can be used for other joints without departing from the aims of the invention.

Figure 1:
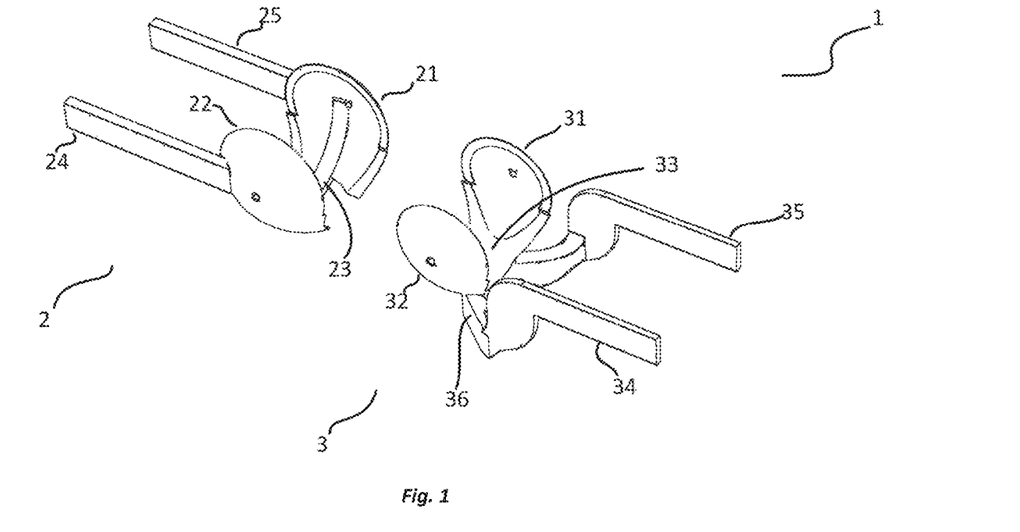
FIG. 1 shows a simplified exploded view of the device according to the invention.

With reference to the appended FIG. 1, the device (1) comprises a first (2) and a second element (3), configured to be assembled by means of a spherical hinge which can be arranged with its own rotation center at the rotation center of the joint to be rehabilitated (for example the elbow).

To such aim, said first element (2) comprises a first (21) and a second spherical shell portion (22) (spherical caps), opposite to each other. Said spherical caps (21, 22) are joined by means of a joining means (23) positioned not to hinder the joint movement. Conveniently, in case of the elbow, said element (23) can be positioned at the rear portion of the arm.

Each one of said caps (21, 22) is then connected to a relative bar (24, 25) configured to be fastened to the limb (for example the arm), according to what described in the detail in the following.

Similarly, said second element (3) comprises a first (31) and a second spherical shell portion (32) (spherical caps), opposite to each other. Said spherical caps (31, 32) are joined by means of a joining element (33) positioned not to hinder the joint movement. Conveniently, in case of the elbow, said element (33) can be arranged at the rear portion of the forearm.

It is to be specified, with reference to the appended figures, that by indicating that each element (2, 3) comprises a first (21, 31) and a second spherical shell portion (22, 32), "opposite to each other" it is meant that the first and second spherical shell portion of each one of the two elements are firmly connected to each other and configured so that they are positioned on opposite portions of the joint when the device (1) is worn.

Moreover, it is to be specified that while coupling said elements by means of spherical hinge, the first spherical shell portion (21) of the first element is coupled with the first spherical shell portion (31) of the second element (3), and the second spherical shell portion (22) of the first element (2) is coupled with the second spherical shell portion of the second element (3).

Each one of said caps (31, 32) is then connected to a relative bar (34, 35) configured to be fastened to the limb (for example the arm), according to what described in detail in the following. Said second element (3) can comprise further abutting means (36), configured to limit the relative rotations allowed along one or more axes when the device is assembled. In this way, hyper-extensions or excessive torsions can be avoided. Preferably, the first element (2) comprises adjusting means (26) which allow to adjust the maximum angle of relative rotation to which said abutting means (36) begin to function. As a way of example, said adjusting means (26) can comprise a screw (26) configured to stop said abutting means (36).

Figure 2:
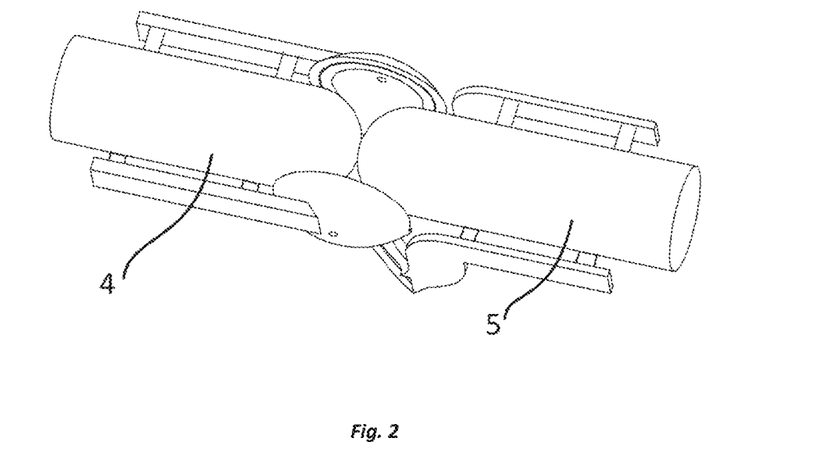
FIGS. 2 and 3 show the device according to the invention with highlighted the geometry of the overall dimensions of the distal and proximal part of a limb.

In FIG. 2, it is shown the device assembled, and inside it an arm (4) and a forearm (5) are schematically shown.

In order to be coupled, according to what shown in FIG. 2, said spherical shell portions (21, 22, 31, 32) are configured so that the outer surface of the shell (31, 32) of said second element (3) can constitute a spherical hinge with the inner surface of the shell (21, 22) of said first element (2).

Figure 3:
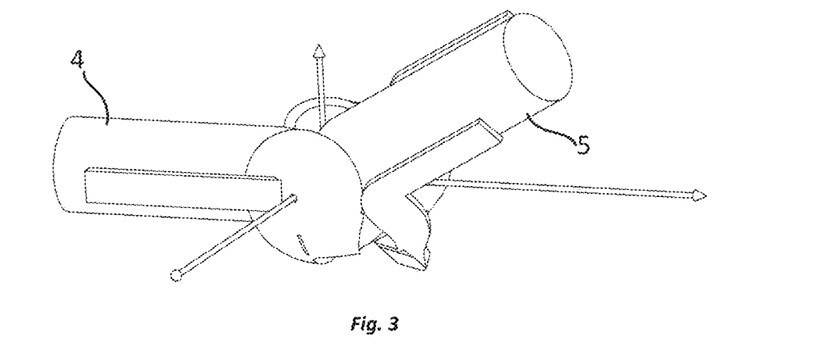

This hinged coupling forces said second element (3) to rotate with respect to said first element (2) only with respect to axes passing through the center of said coupling. In other words, only relative movements obtainable by means of a composition of rotations around the three axes (x, y, z), shown in FIG. 3, are allowed between said first (2) and second element (3).

As yet said, the amplitude of the relative movements allowed according to various axes can be limited configuring suitably the geometry of said abutting means (36), or by providing suitable reliefs and projections on said spherical shell portions.

Yet, as it is clear from FIG. 2, the space comprised between the outer (21, 22) and inner spherical shell portions (31, 32) has to be such that the limb, object of rehabilitation (for example arm and forearm, with the elbow positioned at the center of the spherical hinge, is received therein.

As yet said, each element (2, 3) is provided with bars (24, 25, 34, 35) for fastening the same to the relative proximal or distal portion of the interested limb (for example arm, forearm.

Conveniently, said bars are telescopic, each one provided with a first and a second portion sliding with respect to their own axis, the first portion being integral to the spherical shell and the second portion being movable with respect to the same. In order to minimize frictions, suitable coupling means, such for example linear ball bearings, can be used for realizing the telescopic bars.

Figure 6:
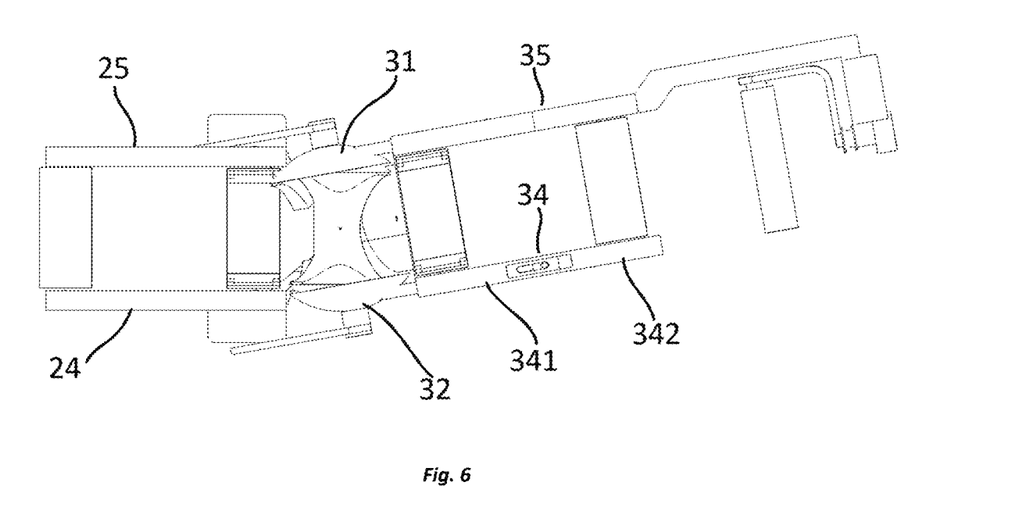

This is shown in FIG. 6 with reference to the first (341) and second portion (342) of the bar (34) It is the same for the other connection bars.

So, fastening means of the type known per seé, such bracelets (27, 37), strings or other ones, are used to fasten the movable portion of each bar to the arm, or, respectively the forearm.

Moreover, preferably, said fastening means (27, 37) are fastened adjustably to said bars, so that they can be adapted to the dimensions of the limb of the patient. Said adjustment can be conveniently carried out by means of elongated holes (271, 371), which allow the bracelets to slide with respect to the bars.

Moreover, preferably, at least one of said fastening means (27, 37) is configured to allow the rotation of the semi-limb around its own axis (for example so to allow the rotation of the forearm around its own axis. To such aim, said fastening means are preferably realized with a first portion fastened to the relative bar and a second portion fastened to said first portion and configured so that it can rotate with respect to the axis of the fastened semi-limb (for example forearm).

After describing the elements, which constitute the device according to the invention at least from a strictly kinematic point of view, its functioning can be described now.

In order to wear the support, the arm (4) is fastened to the telescopic portion of said first element (2), and the forearm (5) to the telescopic portion of said second element, by positioning the elbow at the center of the spherical hinge.

At this point, while carrying out the movement, the spherical hinge will tend spontaneously to be positioned with respect to the telescopic portions fastened to the arm and forearm, so that its own rotation center is kept aligned with the instantaneous rotation center of the joint.

Preferably, but not limitingly, the device comprises further actuation means which allow to exert a couple between said first (2) and second element (3), so that the patient is helped to carry out a complete extension of the limb. Conveniently, said actuation means exert said couple only when the relative angular position of the first and second element exceeds a determined angle, which can be adjusted. In this way, the patient is forced to carry out the first portion of the movement with no outer help, and he is helped only to carry out the end portion of the extension movement. While the therapy proceeds, and while the patient conditions improve, the angle to which said actuation means intervene can be adjusted so that the amplitude of the movement the patient carries out by himself increases.

Figure 7:
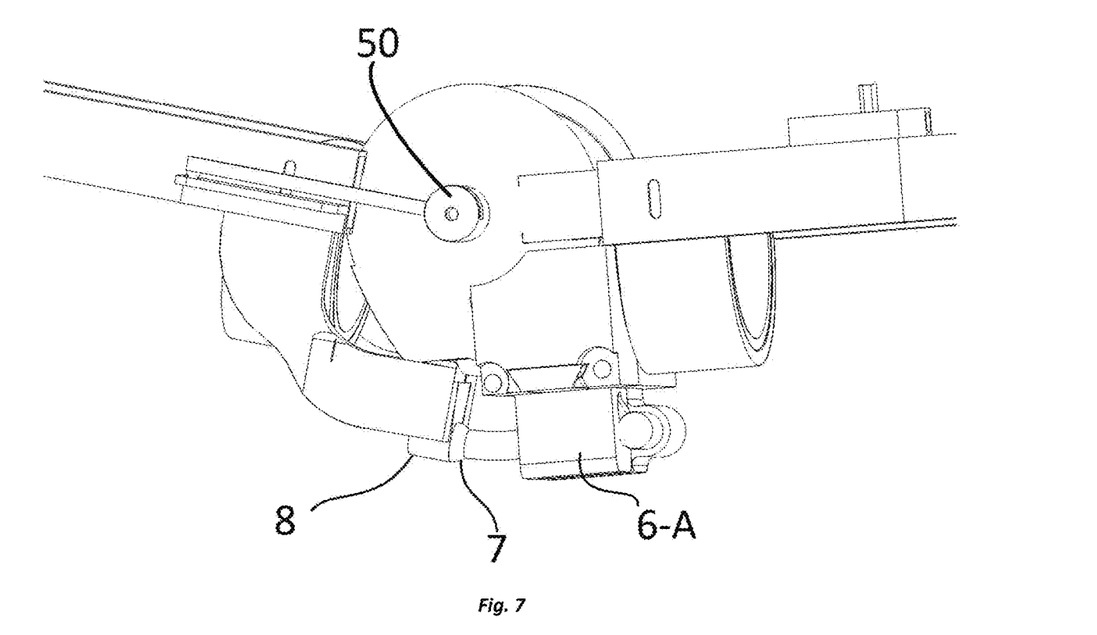
FIG. 7 shows the position of the angular position sensor
Figure 8:
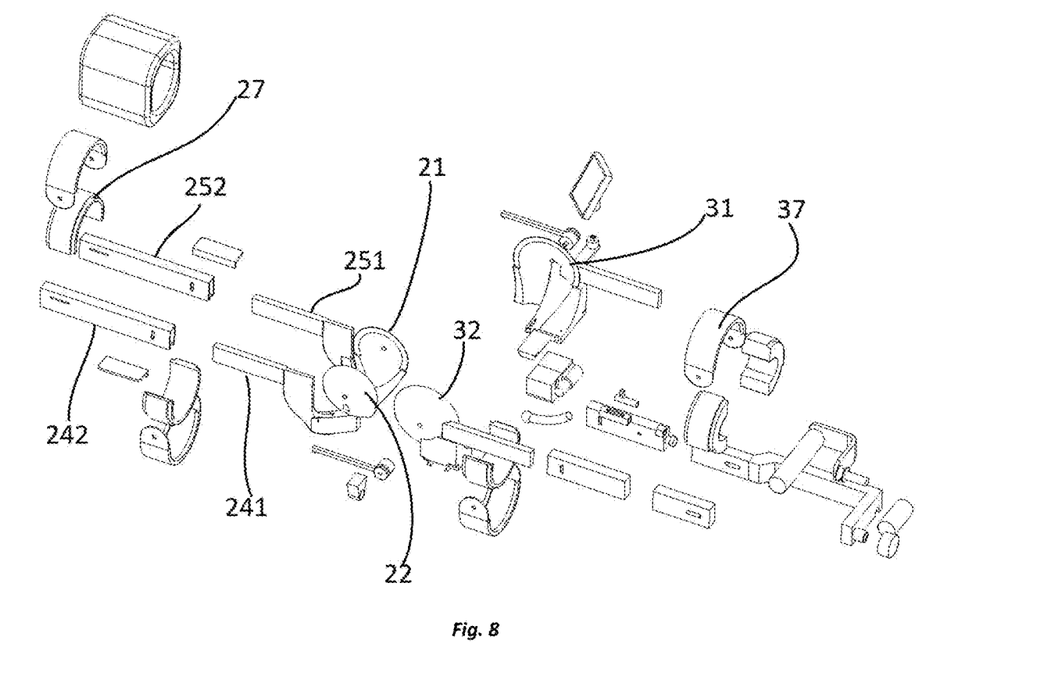
FIG. 8 shows an exploded view of the device.

A first embodiment of said actuation means is shown in FIG. 7, in which a ferromagnetic core (7) is shown, fastened to said second element (3) so that by means of a motor (6B) its position can be varied. The second element (3) comprises also an electromagnet (6-A) configured to magnetize, when supplied with current, said ferromagnetic core (7). A permanent magnet (8) is positioned on the first element (2). The system is configured so that by varying the position of said ferromagnetic core the angle can be varied to which said permanent magnet exerts an attraction action which helps the patient to carry out the movement. By acting on the tension applied to the electromagnet (6-A), on the polarity, on the current and on the time of supplying the same, a whole control on the position is obtained to which the couple is applied, on its intensity and duration.

Figure 9:
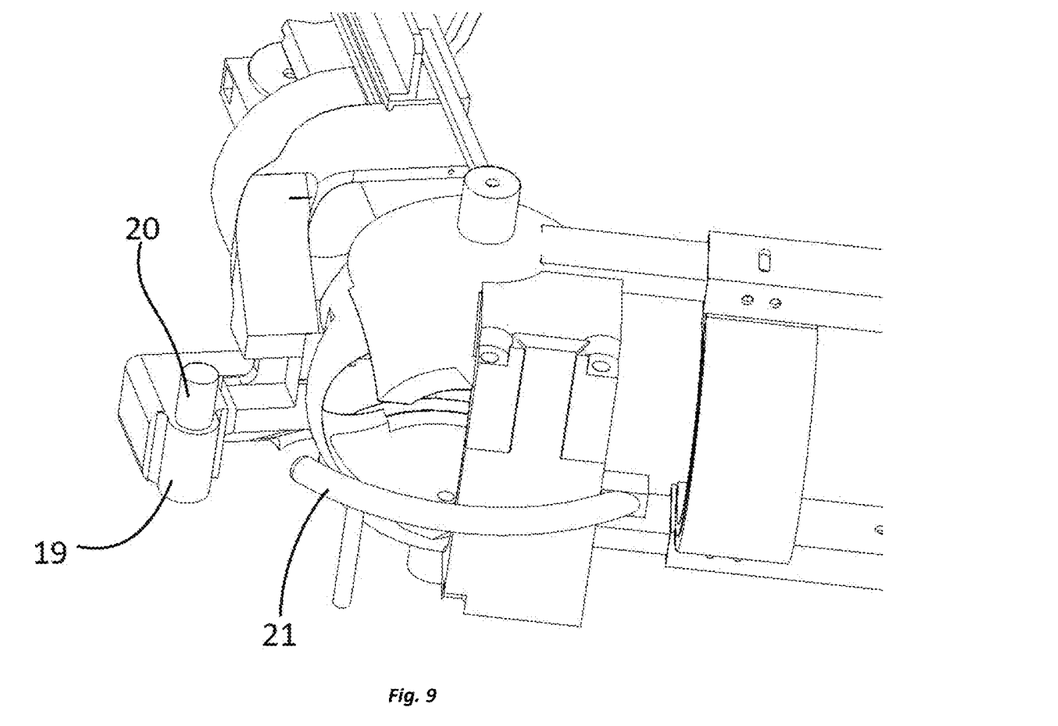
FIGS. 9 and 10 show the position of the motor and the gear wheel.
Figure 10:
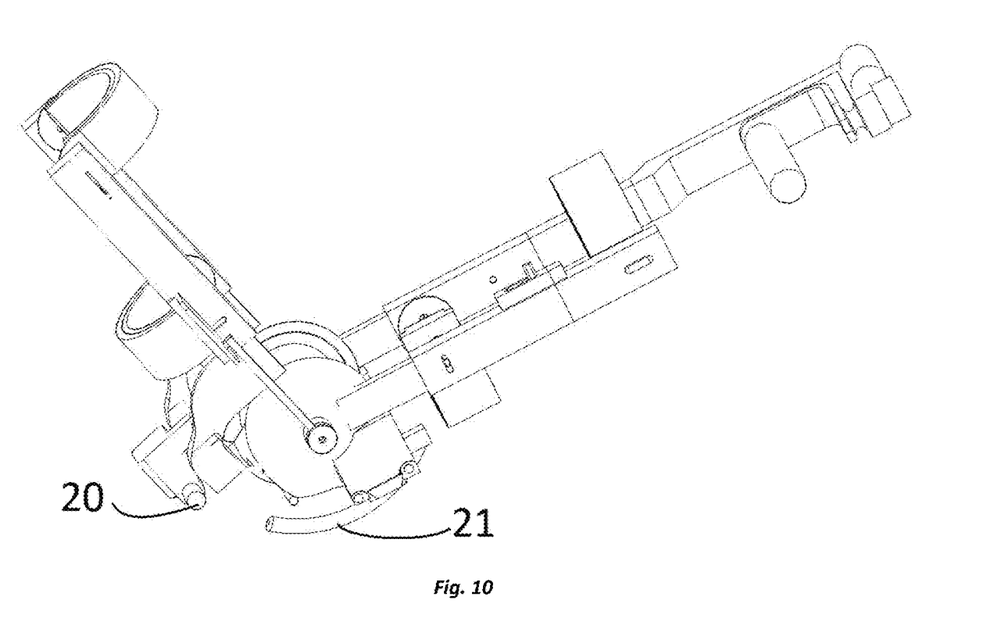

According to another embodiment shown in FIG. 9, the actuation means can comprise a motor (19) which puts in rotation a wheel (20), configured to act on a guide (29). The motor (19) and the guide (29) are respectively integral to the first and second element (2, 3), and are configured so that when the wheel (20) engages the guide (29), this one exerts an action apt to increase the opening angle of the device. According to a first embodiment, the wheel (20) is a toothed wheel, and the guide (29) is provided with teeth configured to engage said wheel. According to another embodiment, the wheel (20) acts by friction, and the device comprises a pre-tensioning system configured to push the motor and the wheel towards said guide (29) by means of a spring.

Moreover, preferably, the device comprises at least an angular position sensor (50), and preferably it comprises two angular position sensors arranged on opposite sides of said spherical hinge, configured to detect the angle formed between said first and second element, as well as means for acquiring data detected by said sensors and data processing means configured to detect and save the information detected by said angular position sensors while the device is used.

Figure 17:
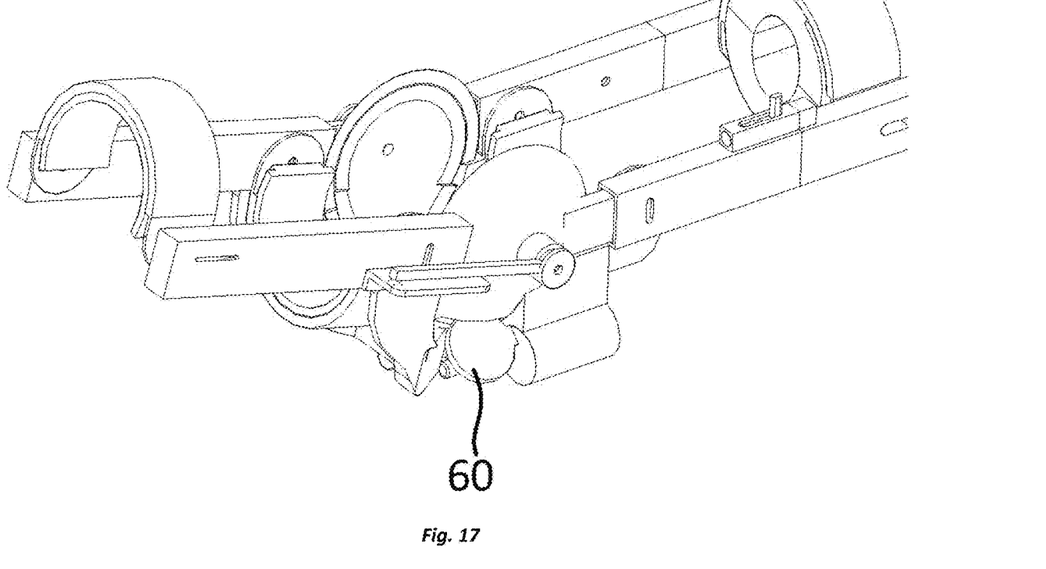
FIGS. 17 to 19 show an embodiment which makes use of two motorized wheels.
Figure 18:
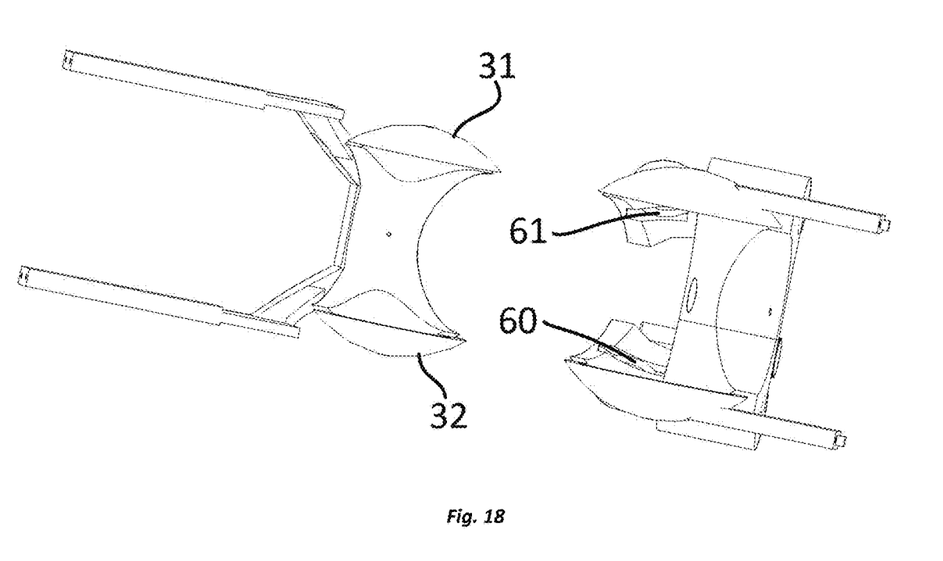
Figure 19:
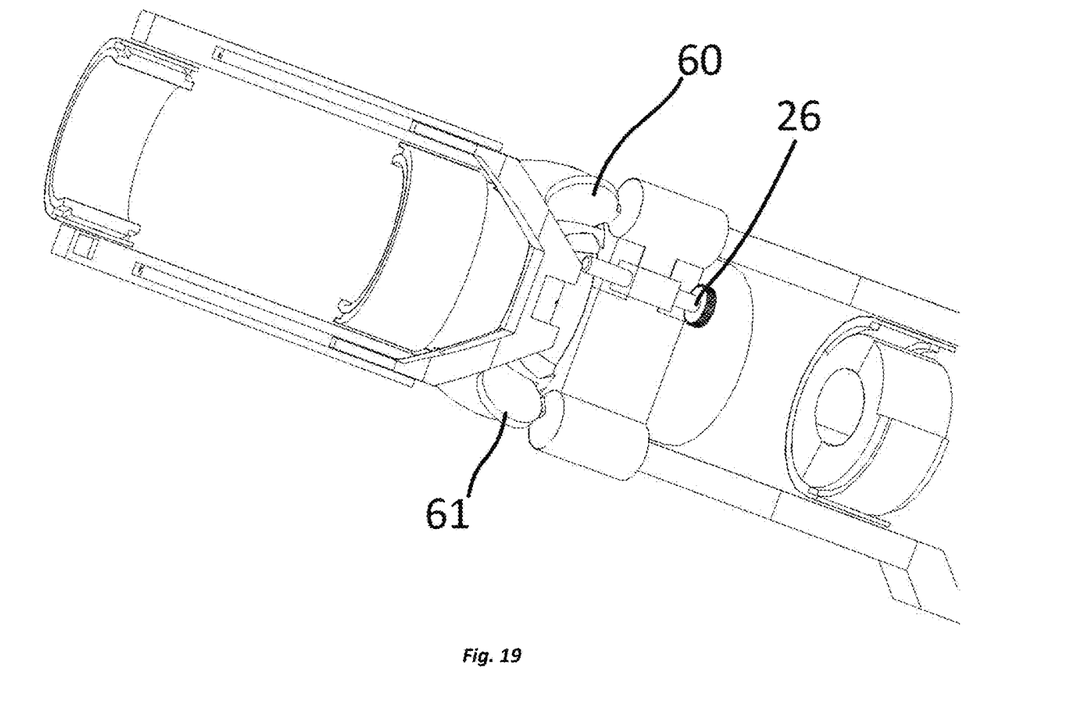

According to another embodiment, the device comprises two motorized wheels (60, 61) integral to said outer spherical shell portion and configured so to act on said inner spherical shell portion, preferably by friction. The wheels (60, 61) are positioned on opposite portions with respect to the middle of the device, and are configured so that, by controlling respective motors so that the wheels (60, 61) rotate with the same movement speed the resulting movement is a pure flexion-extension, while by controlling the motors so that the wheels rotate at different speed, the resulting movement is a combination of flexion/extension and lying on one's stomach/on one's back movements. Very briefly, during the rehabilitation movement it is possible to impose a desired dotation of the forearm around its own axis by controlling the rotation speed of the two wheels (60, 61) Preferably, the device will comprise also angular position sensors configured to measure both the flexion/extension angle and the lying on one's stomach/on one's back angle.

Figure 4:
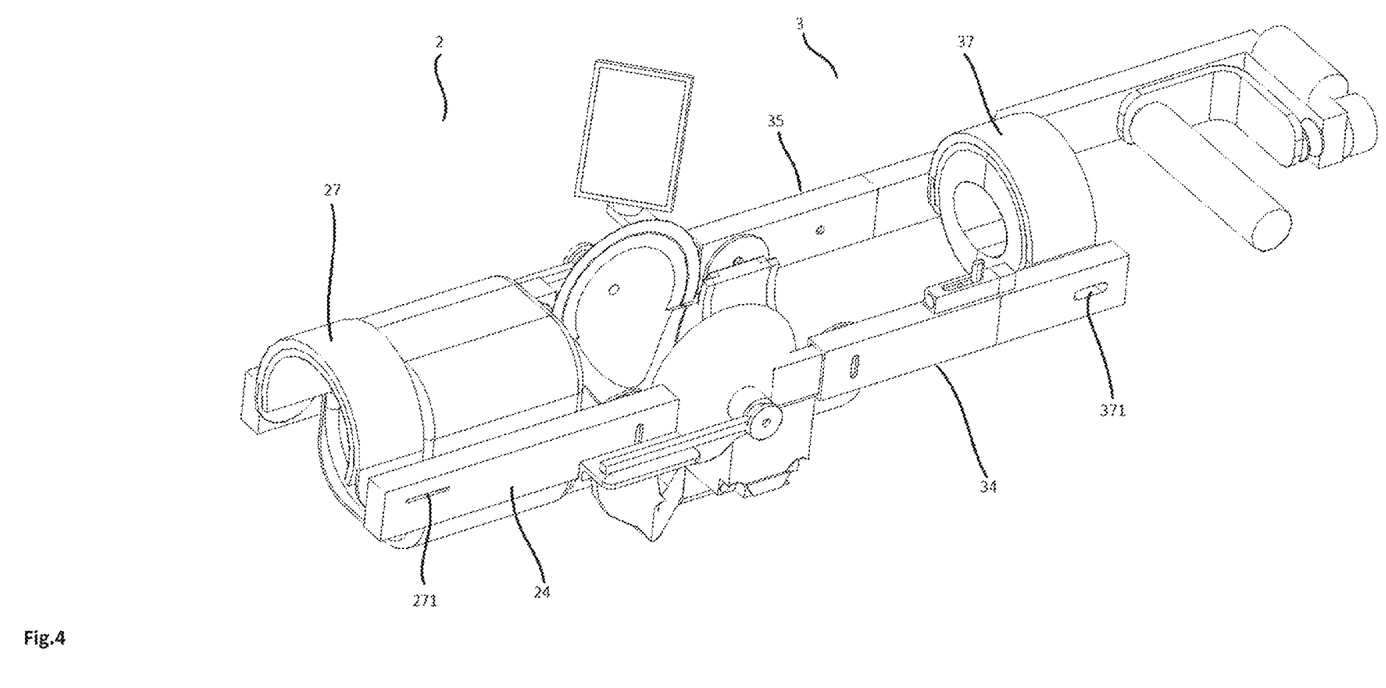
FIG. 4 shows an assembled view of the device.
Figure 5:
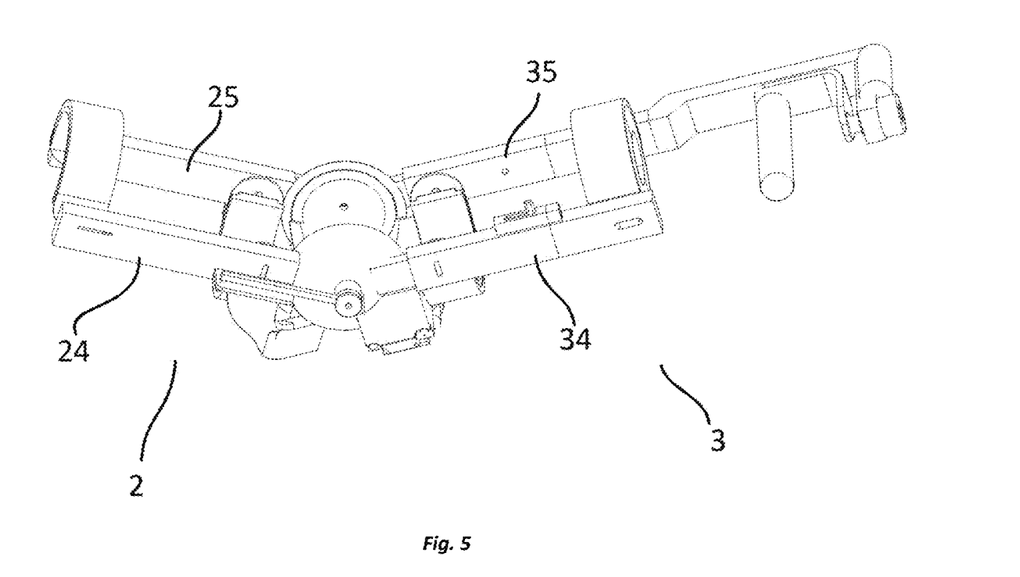
FIGS. 5 and 6 show views of the device showing the construction details of the brackets.
Figure 11:
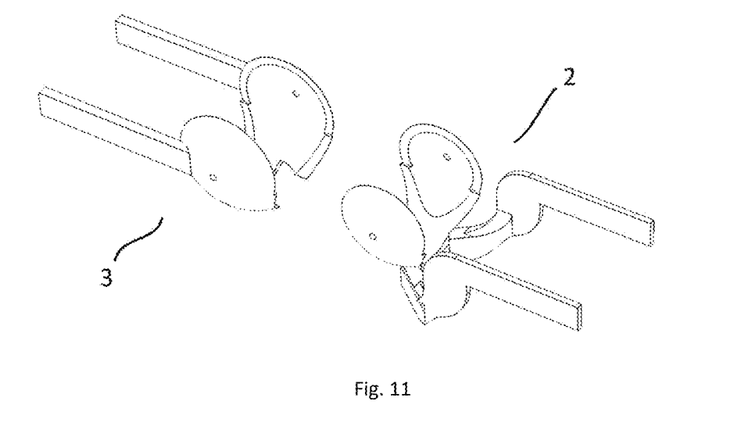
FIGS. 11 to 15 show the steps for assembling the two parts that make up the device.
Figure 12:
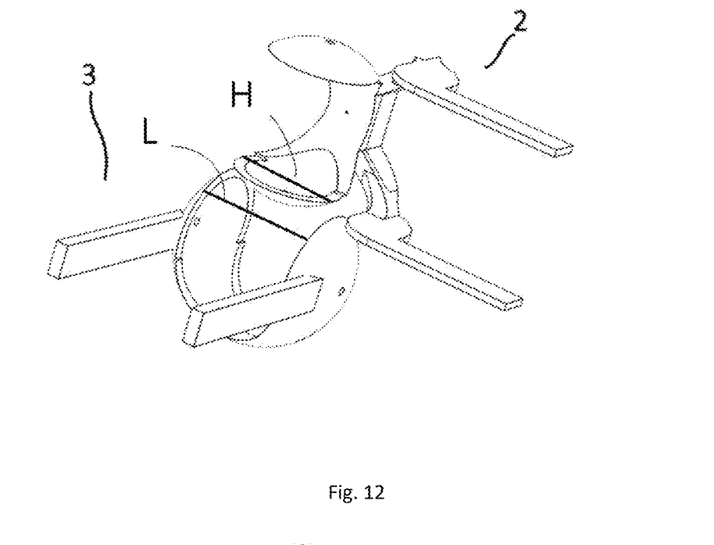

Without this being limiting for the aims of the invention, FIG. 4 shows an embodiment in which the mechanism assembly is particularly facilitated. In particular, the assembly described in the following is possible if the base diameter (H) of the minor spherical cap is lower than the distance (L) between the two caps of the outer shell. With these conditions, the assembly is possible according to what described in the following; figures:

FIG. 11: the second element (3) is out of the first element, rotated with respect to its end position;

FIG. 12: the second element enters by means of simple translation the first element.

Figure 13:
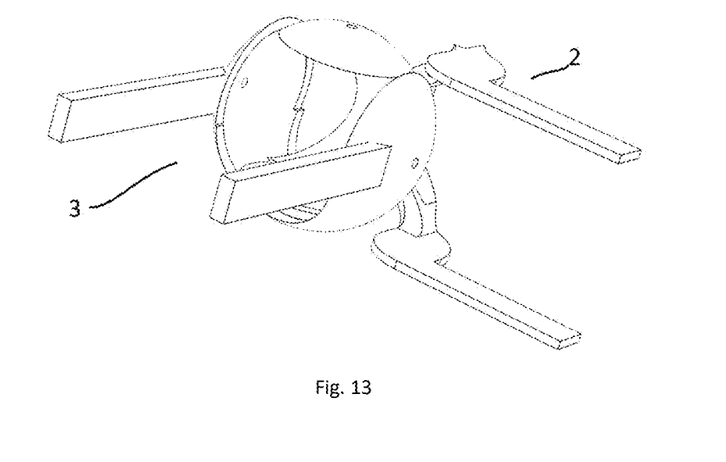
Figure 14:
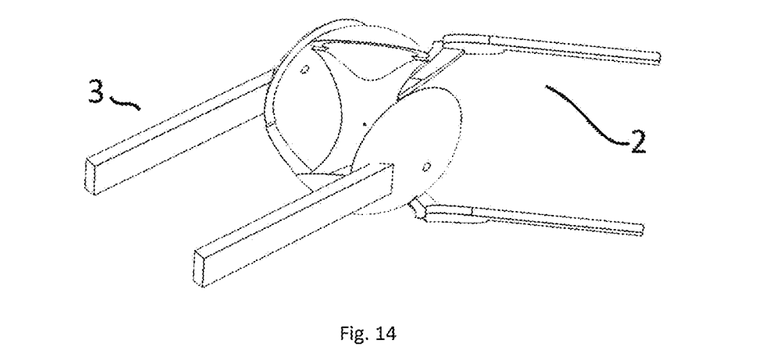
Figure 15:
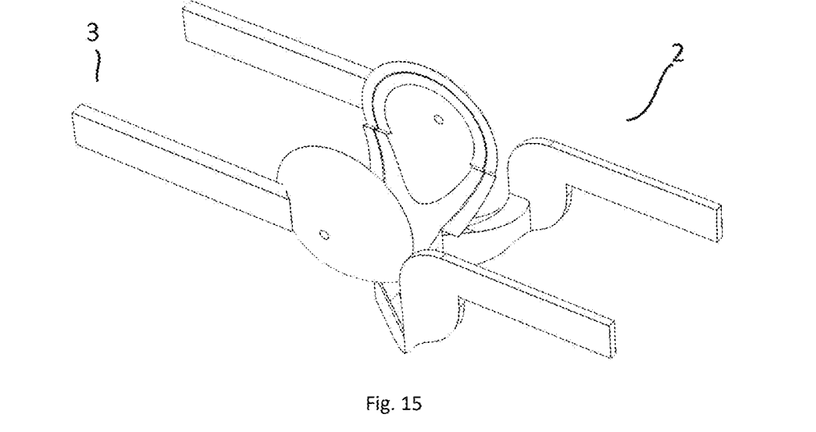

FIG. 13: a simple rotation of the second element (3) allows to put the device in its working position.

It is to be noted that in the end position the two semi-hinges cannot be extracted except by an inverted movement with respect to the just described one, which, clearly, is not possible when the device is worn.

Figure 16:
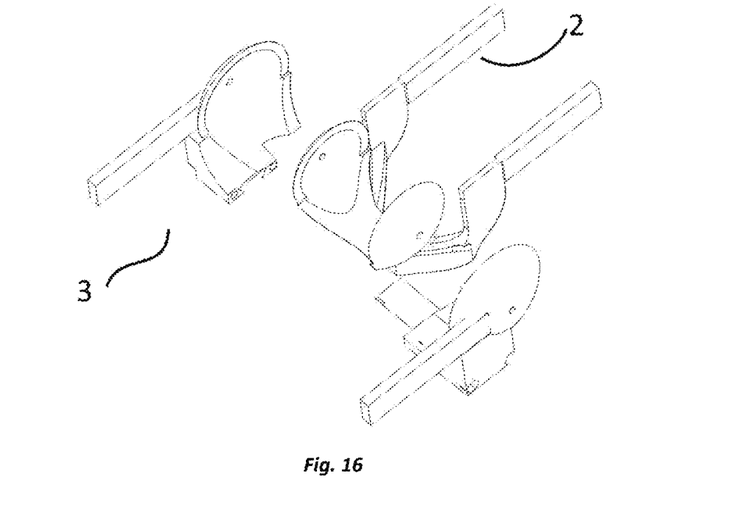
FIG. 16 shows the device with one of the two parts disassembled.

An alternative embodiment provides that at least a first element (2) is realized in two portions which can be disassembled from each other, which so can be re-assembled after positioning the second element (3) thereinside.

Yet, according to another embodiment the device according to the invention can comprise relative blocking means of the two spherical shells in a determined position, configured to allow to immobilize the limb of the patient. In this way, the device can be also substituted by casts or other kinds of immobilizing bandages known at the state of the art.

According to another embodiment, the device comprises further:

linear actuators configured to control said telescopic bars;

actuators for controlling said at least fastening means (27, 37) configured to allow the rotation of the semi-limb around its own axis;

position detecting means, able to acquire the relative position of the elements controlled by said actuators;

electronic control and actuating means, able to acquire the signal acquired by said detecting means and to control said actuators.

acquiring means of an outer instruction by the user (for example acquiring means of electromyographic signals).

Conveniently, the device comprising said other elements can be used as exoskeleton, with rehabilitation or support function for increasing the lifting force of the person wearing it.

To such end, conveniently the usage as exoskeleton occurs by means of a first learning step, in which the user carries out, without load, the lifting movement and said control means acquire the position variation in time as detected by each one of said position detecting means.

In a second step of movement execution, said electronic means control said actuators such that each one covers the same trajectory.

The movement start or stop instruction is sent by said electronic means to said actuators as a function of the signal detected by said acquiring means of an outer instruction by the user (for example acquiring means of electromyographic signals).

The invention claimed is:

1. A device (1) for articular rehabilitation comprising a first element (2) provided with bars (24, 25) for fastening to a proximal portion of a limb and a second element (3) provided with bars (34, 35) for fastening to a distal portion of the limb, said first element (2) comprising a first (21) and a second spherical shell portion (22) opposite to each other, and said second element (3) comprising a first (31) and a second spherical shell portion (32) opposite to each other, said spherical shell portions (21, 22, 31, 32) being configured to fasten said first and second elements by means of a spherical hinge coupling so that only relative movements obtainable by means of a composition of rotations around three axes passing through a center of said shell portions are allowed between said first (2) and second element (3) and being configured so that the space comprised inside said spherical shell portions (21, 22, 31, 32), when coupled, is such that a joint object of the rehabilitation is allowed to be received therein, said first (21, 31) and second spherical shell portions (22, 32) of each one of the two elements (2, 3) being firmly connected to each other and configured to be positioned on opposite portions of the joint when said device (1) is worn, said first spherical shell portion (21) of said first element (2) being configured to be coupled with said first spherical shell portion (31) of said second element (3), and said second spherical shell portion (22) of said first element (2) being configured to be coupled with said second spherical shell portion (32) of said second element (3); and wherein the device (1) further comprises an actuation ferromagnetic core (7) which allows exerting a torque between said first (2) and second element (3), so that a patient is helped to carry out a complete extension of the limb; and wherein said actuation ferromagnetic core (7) comprises two motorized wheels (60, 61) integral to said outer spherical shell portion and configured to act on said inner spherical shell portion, positioned on opposite portions with respect to a middle of the device, and configured so that said actuation ferromagnetic core (7) imposes a desired amount of lying on one's stomach or on one's back movement during a flexion-extension movement, by controlling a rotation speed of a respective motor.

2. The device (1) for articular rehabilitation according to claim 1, wherein any two of said bars (34, 35) are telescopic, each provided with a first and a second portion sliding with respect to their own axis, one of said portions being fixed to the relative spherical shell portion and the other one of said portions being movable with respect to the relative spherical shell portion, so that said joint can be positioned at the center of rotation of said spherical hinge during flexion and extension movements of said limb, said device further comprising adjustable fastening loops (27, 37) to fasten the movable portion of each bar to the proximal or, respectively, a distal portion of the limb, and wherein at least one of said adjustable fastening loops (27, 37) is configured to allow the rotation of a semi-limb around its own axis.

3. The device (1) for articular rehabilitation according to claim 2, further comprising constraint loops for fastening the movable portion of each bar to said distal or proximal portion of said limb.

4. The device (1) for articular rehabilitation according to claim 1, wherein said second element (3) has a spherical cap having a diameter (H) of a base which is lower than a distance (L) between the two spherical shell portions of said first element (2).

5. The device (1) for articular rehabilitation according to claim 1, wherein said spherical shell portions (22) of said first element (2) can be disassembled from each other, and can be re-assembled after positioning the second element (3) thereinside.

6. The device (1) for articular rehabilitation according to claim 1, wherein said second element (3) further comprises an abutting surface (36), configured to limit the relative rotations allowed along one or more axes, when the device is assembled.

7. The device (1) for articular rehabilitation according to claim 1, wherein said actuation ferromagnetic core (7) exerts said torque only when the relative angular position of the first and second element exceeds a determined angle.

8. The device (1) for articular rehabilitation according to claim 1 wherein said actuation ferromagnetic core (7) is fastened to said second element (3) so that by means of a motor (6B) its position can be varied and an electromagnet (6-A) configured to magnetize, when supplied with current, said ferromagnetic core (7), and in that on said first element (2) a permanent magnet (8) is positioned, and in that the system is configured so that, by varying the position of said actuation ferromagnetic core (7) an angle can be varied at which said permanent magnet (8) exerts an attraction which is configured to help a patient to carry out a movement.

9. The device (1) for articular rehabilitation according to claim 1, further comprising two angular position sensors, arranged on opposite sides of said spherical hinge, configured to detect an angle formed between said first and second element, as well as a controller for acquiring data detected by said sensors and data processing means configured to detect and save the information detected by said angular position sensors while the device is used.

10. The device (1) for articular rehabilitation according to claim 1, wherein any two of said bars are telescopic, and further comprising:
linear actuators configured to control said telescopic bars;
position sensor able to acquire the relative position of the elements controlled by said actuators;
electronic actuation controller able to acquire the signal acquired by said detecting means and to control said actuators,
data input device of an outer instruction by the user.

* * * * *